US012606767B2

(12) United States Patent
Rodgers

(10) Patent No.: US 12,606,767 B2
(45) Date of Patent: Apr. 21, 2026

(54) 1,4-BENZOXAZINE COMPOUNDS AND LUBRICANT COMPOSITIONS CONTAINING THE SAME

(71) Applicant: The Lubrizol Corporation, Wickliffe, OH (US)

(72) Inventor: Zachary L. Rodgers, Tallmadge, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 18/291,349

(22) PCT Filed: Jul. 29, 2022

(86) PCT No.: PCT/US2022/038764
§ 371 (c)(1),
(2) Date: Jan. 23, 2024

(87) PCT Pub. No.: WO2023/009774
PCT Pub. Date: Feb. 2, 2023

(65) Prior Publication Data

US 2025/0115823 A1 Apr. 10, 2025

Related U.S. Application Data

(60) Provisional application No. 63/226,983, filed on Jul. 29, 2021.

(51) Int. Cl.

| | |
|---|---|
| ***C10M 133/50*** | (2006.01) |
| ***C07D 265/38*** | (2006.01) |
| ***C07D 498/04*** | (2006.01) |
| ***C10M 101/00*** | (2006.01) |
| ***C10M 125/22*** | (2006.01) |
| ***C10M 129/50*** | (2006.01) |
| ***C10M 133/12*** | (2006.01) |
| ***C10M 133/44*** | (2006.01) |
| ***C10M 135/04*** | (2006.01) |
| ***C10M 139/00*** | (2006.01) |
| ***C10M 141/12*** | (2006.01) |
| ***C10M 143/12*** | (2006.01) |
| ***C10M 161/00*** | (2006.01) |
| ***C10M 169/04*** | (2006.01) |
| *C10N 10/04* | (2006.01) |

(Continued)

(52) U.S. Cl.
CPC ......... *C10M 133/50* (2013.01); *C07D 265/38* (2013.01); *C07D 498/04* (2013.01); *C10M 101/00* (2013.01); *C10M 125/22* (2013.01); *C10M 129/50* (2013.01); *C10M 133/12* (2013.01); *C10M 133/44* (2013.01); *C10M 135/04* (2013.01); *C10M 139/00* (2013.01); *C10M 141/12* (2013.01); *C10M 143/12* (2013.01); *C10M 161/00* (2013.01); *C10M 169/044* (2013.01); *C10M 2201/06* (2013.01); *C10M 2205/06* (2013.01); *C10M 2207/144* (2013.01); *C10M 2215/064* (2013.01); *C10M 2215/30* (2013.01); *C10M 2219/022* (2013.01); *C10M 2227/00* (2013.01); *C10N 2010/04* (2013.01); *C10N 2020/02* (2013.01); *C10N 2020/067* (2020.05); *C10N 2030/04* (2013.01); *C10N 2030/06* (2013.01); *C10N 2030/10* (2013.01); *C10N 2030/45* (2020.05); *C10N 2030/70* (2020.05); *C10N 2040/04* (2013.01); *C10N 2040/25* (2013.01)

(58) Field of Classification Search
CPC ......................... C10M 133/50; C10M 101/00; C10M 125/22; C10M 129/50; C10M 133/12; C10M 133/44; C10M 135/04; C10M 139/00; C10M 141/12; C10M 143/12; C10M 161/00; C10M 169/044; C10M 2201/06; C10M 2205/06; C10M 2207/144; C10M 2215/064; C10M 2215/30; C10M 2219/022; C10M 2227/00; C10M 2290/02; C07D 265/38; C07D 498/04; C10N 2010/04; C10N 2020/02; C10N 2020/067; C10N 2030/04; C10N 2030/06; C10N 2030/10; C10N 2030/45; C10N 2030/70; C10N 2040/04; C10N 2040/25
See application file for complete search history.

(56) References Cited

U.S. PATENT DOCUMENTS

| | | | |
|---|---|---|---|
| 2,483,838 A | 10/1949 | Niederl | |
| 3,172,892 A | 3/1965 | Le Suer et al. | |

(Continued)

FOREIGN PATENT DOCUMENTS

| | | | |
|---|---|---|---|
| EP | 0355895 | 1/1991 | |
| EP | 1308496 A2 * | 5/2003 | .......... C10M 141/00 |

(Continued)

OTHER PUBLICATIONS

Luke A. Farmer et al., "Phenoxazine: A Priviledged Scaffold for Radical-Trapping Antioxidants", The Journal of Organic Chemistry, Published Sep. 8, 2017, 82, pp. 10523-10536.

*Primary Examiner* — Cephia D Toomer
(74) *Attorney, Agent, or Firm* — Joseph A. Svarovsky; Michael A. Miller

(57) ABSTRACT

The disclosed technology relates to compositions suitable for use as lubricants and lubricant additive compositions which comprise a 1,4-benzoxazine-derived antioxidant, wherein the antioxidant itself may also be described as a 1,4-benzoxazine compound, and optionally comprising other additives suitable for lubricants, such as an anti-wear agent, a detergent, or a dispersant.

14 Claims, No Drawings

(51) Int. Cl.

| | |
|---|---|
| *C10N 20/00* | (2006.01) |
| *C10N 20/02* | (2006.01) |
| *C10N 30/00* | (2006.01) |
| *C10N 30/04* | (2006.01) |
| *C10N 30/06* | (2006.01) |
| *C10N 30/10* | (2006.01) |
| *C10N 40/04* | (2006.01) |
| *C10N 40/25* | (2006.01) |

(56) References Cited

U.S. PATENT DOCUMENTS

| | | | | |
|---|---|---|---|---|
| 4,234,435 | A | 11/1980 | Meinhardt et al. | |
| 4,863,623 | A | 9/1989 | Nalesnik | |
| 5,840,663 | A * | 11/1998 | Nibert | C10M 163/00 508/438 |
| 6,107,257 | A | 8/2000 | Valcho et al. | |
| 6,107,258 | A | 8/2000 | Esche, Jr. et al. | |
| 6,117,825 | A | 9/2000 | Liu et al. | |
| 7,285,516 | B2 | 10/2007 | Carrick et al. | |
| 7,407,919 | B2 | 8/2008 | Wilk et al. | |
| 7,615,521 | B2 | 11/2009 | Eveland et al. | |
| 8,067,347 | B2 | 11/2011 | Ruhe, Jr. et al. | |
| 8,557,753 | B2 | 10/2013 | Gieselman et al. | |
| 8,637,437 | B2 | 1/2014 | Gieselman et al. | |
| 2020/0010776 | A1 * | 1/2020 | Pratt | C10M 169/04 |

FOREIGN PATENT DOCUMENTS

| | | | |
|---|---|---|---|
| EP | 3085757 | | 10/2016 |
| GB | 776669 | * | 6/1957 |
| WO | 20060015130 | | 2/2006 |
| WO | 20060047486 | | 5/2006 |
| WO | 20080147704 | | 12/2008 |
| WO | 20180165760 | | 9/2018 |

* cited by examiner

1,4-BENZOXAZINE COMPOUNDS AND LUBRICANT COMPOSITIONS CONTAINING THE SAME

CROSS REFERENCE TO RELATED APPLICATION

This application claims priority from PCT Application Serial No. PCT/US2022/038764 filed on Jul. 29, 2022, which claims the benefit of U.S. Provisional Application No. 63/226,983 filed on Jul. 29, 2021, both of which are incorporated in their entirety by reference herein.

FIELD

The disclosed technology relates to compositions suitable for use as lubricants and lubricant additive compositions which comprise a 1,4-benzoxazine-derived antioxidant, wherein the antioxidant itself may also be described as a 1,4-benzoxazine compound, and optionally comprising other additives suitable for lubricants, such as an anti-wear agent, a detergent, or a dispersant.

BACKGROUND

Antioxidants are an important class of additives since they are used to provide and/or improve the anti-oxidation performance of organic compositions, including lubricant compositions that contain organic components, by preventing or retarding oxidative and thermal decomposition. Antioxidants in some applications can result in an increase in volatility which can be undesirable due to required environmental regulations and/or performance standards.

It is known to use substituted diarylamine compounds in an oil of lubricating viscosity to reduce oxidation breakdown and improve cleanliness.

The subject matter described herein provides an ashless antioxidant which has suitable performance properties when used in lubricant formulations, especially for heavy duty diesel engines and passenger car crankcase engines, for example, and which may also reduce regulatory concerns.

SUMMARY

Provided is a lubricating composition comprising an oil of lubricating viscosity and a 1,4-benzoxazine compound. In certain embodiments, the 1,4-benzoxazine compound is an ashless 1,4-benzoxazine compound. In certain embodiments, provided is a lubricating composition comprising an oil of lubricating viscosity and an ashless antioxidant, wherein the ashless antioxidant comprises a 1,4-benzoxazine compound. In certain embodiments, provided is a lubricating composition comprising an oil of lubricating viscosity and an ashless antioxidant, wherein the ashless antioxidant consists essentially of a 1,4-benzoxazine compound. In certain embodiments, provided is a lubricating composition comprising an oil of lubricating viscosity and an ashless antioxidant, wherein the ashless antioxidant consists of a 1,4-benzoxazine compound. In certain embodiments, provided is a lubricating composition comprising an oil of lubricating viscosity and an ashless antioxidant, wherein the ashless antioxidant is a 1,4-benzoxazine compound.

The present subject matter further provides for lubricating compositions suitable for lubricating an internal combustion engine, comprising: (A) a major amount of an oil of lubricating viscosity; (B) a minor amount of at least one antioxidant comprising a 1,4-benzoxazine compound, as described herein; and (C) a minor amount of at least one other additive comprising at least one of viscosity modifiers, pour point depressants, dispersants, detergents, anti-wear agents, antioxidants different from the antioxidant of component (B), friction modifiers, corrosion inhibitors, seal swell agents, metal deactivators, or foam inhibitors.

The present subject matter further provides methods of lubricating an internal combustion engine, wherein the methods comprise the step of supplying to the engine any of the lubricating compositions described herein. Such methods may include a method for improving the oxidative stability of an engine oil lubricant (e.g., a crankcase lubricant).

The present subject matter further provides a method for lubricating an internal combustion engine, comprising: (A) supplying to said engine a lubricating composition comprising: (i) an oil of lubricating viscosity; (ii) a minor amount of at least one antioxidant comprising a 1,4-benzoxazine compounds, as described herein; and (iii) a minor amount of at least one other additive comprising at least one of viscosity modifiers, pour point depressants, dispersants, detergents, anti-wear agents, antioxidants that are different from the antioxidant of component (ii), friction modifiers, corrosion inhibitors, seal swell agents, metal deactivators, or foam inhibitors.

DETAILED DESCRIPTION

Various features and embodiments of the present subject matter will be described below by way of non-limiting illustration.

The amount of each chemical component described herein is presented exclusive of any solvent or diluent oil, which may be customarily present in the commercial material, that is, on an active chemical basis, unless otherwise indicated. Unless otherwise indicated, each chemical or composition referred to herein should be interpreted as being a commercial grade material which may contain the isomers, byproducts, derivatives, and other such materials which are normally understood to be present in the commercial grade.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring); substituted hydrocarbon substituents, that is, substituents containing non-hydrocarbon groups which, in the context of the present subject matter, do not alter the predominantly hydrocarbon nature of the substituent (e.g., halo (especially chloro and fluoro), hydroxy, alkoxy, mercapto, alkylmercapto, nitro, nitroso, and sulfoxy); hetero substituents, that is, substituents which, while having a predominantly hydrocarbon character, in the context of the present subject matter, contain other than carbon in a ring or chain otherwise composed of carbon atoms and encompass substituents as pyridyl, furyl, thienyl and imidazolyl. Heteroatoms include sulfur, oxygen, and nitrogen. In general, no more than two, or no more than one, non-hydrocarbon substituent will be present for every ten carbon atoms in the hydrocarbyl group; alternatively, there may be no non-hydrocarbon substituents in the hydrocarbyl group.

It is known that some of the materials described above may interact in the final formulation, so that the components of the final formulation may be different from those that are initially added. For instance, metal ions (of, e.g., a detergent) may migrate to other acidic or anionic sites of other molecules. The products formed thereby, including the products formed upon employing the composition of the present subject matter in its intended use, may not be susceptible of easy description. Nevertheless, all such modifications and reaction products are included within the scope of the present subject matter; the present subject matter encompasses the composition prepared by admixing the components described herein.

As used herein, the indefinite article "a"/"an" is intended to mean one or more than one. As used herein, the phrase "at least one" means one or more than one of the following terms. Thus, "a"/"an" and "at least one" may be used interchangeably. For example "at least one of A, B or C" means that just one of A, B or C may be included, and any mixture of two or more of A, B and C may be included, in alternative embodiments.

As used herein, the term "substantially" means that a value of a given quantity is within ±10% of the stated value. In other embodiments, the value is within +5% of the stated value. In other embodiments, the value is within +2.5% of the stated value. In other embodiments, the value is within ±1% of the stated value.

As used herein, the term "substantially free of" means that a component does not include any intentional addition of the material which the component is "substantially free of". For example, the component may include a material which the component is "substantially free of" at no more than impurity levels, which may be the result of incomplete chemical reactions and/or unintended/undesired (but perhaps unavoidable) reaction products.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

The present subject matter relates to lubricating compositions comprising an oil of lubricating viscosity and an ashless antioxidant, wherein the ashless antioxidant comprises a 1,4-benzoxazine compound, and methods of using such lubricating compositions, such as methods of lubricating internal combustion engines utilizing such antioxidants. The lubricating compositions may include further lubricant additives as described herein.

The lubricating compositions described herein may find use in various applications as a lubricant composition for: internal combustion engines, including gasoline engines or spark-ignited engines, such as passenger car engines, diesel engines, or compression-ignited engines, such as heavy duty diesel truck engines, natural gas fueled engines, such as stationary power engines, two-cycle engines, aviation piston engines and turbine engines, marine and railroad diesel engines; power transmissions such as automatic transmission, transaxle transmissions, or farm tractor transmissions; gears, such as industrial gears or automotive gears; metalworking; hydraulic systems; special applications, such as bearings, which may require that the lubricating composition be a grease; and hydrocarbon fuels for an internal combustion engine such as a gasoline or diesel fuel.

One component of the lubricating compositions disclosed herein is an oil of lubricating viscosity. As used herein, an oil of lubricating viscosity may include natural and/or synthetic oils, oils derived from hydrocracking, hydrogenation, and/or hydrofinishing, unrefined oils, refined oils, re-refined oils or mixtures thereof. A more detailed description of unrefined oils, refined oils, and re-refined oils is provided in WO 2008/147704 A1, paragraphs [0054] to [0056]. A more detailed description of natural and synthetic lubricating oils is found in paragraphs [0058] and [0059] respectively of WO 2008/147704 A1. Synthetic oils may also be produced by Fischer-Tropsch reactions and may be hydroisomerized Fischer-Tropsch hydrocarbons or waxes. In certain embodiments, oils may be prepared by a Fischer-Tropsch gas-to-liquid synthetic procedure, as well as other gas-to-liquid procedures.

Suitable oils may be produced from biological (i.e., natural) sources or by bio-engineered processes. This includes both naturally-occurring oils, such as vegetable oils and triglyceride oils, which may be further refined or purified by standard processes, and those oils that may be derived by biological conversion of a natural chemical into oil directly or by bio-formation of building block pre-cursor molecules capable of being further converted into oil by known processes.

Oils of lubricating viscosity may also be defined as specified in the April 2008 version of "Appendix E—API Base Oil Interchangeability Guidelines for Passenger Car Motor Oils and Diesel Engine Oils", section 1.3 Subheading 1.3. "Base Stock Categories". The API Guidelines are also summarized in U.S. Pat. No. 7,285,516 B2 (see column 11, line 64 to column 12, line 10).

In certain embodiments, the oil of lubricating viscosity may be an API Group I, Group II, Group III, or Group IV mineral oil, an ester or other synthetic oil, or any mixtures thereof.

The amount of the oil of lubricating viscosity present in the lubricating compositions described herein, is generally the balance remaining after subtracting from 100 weight percent the sum of the amount of the dispersant additive package according to the present disclosure and additional additives, if any. As such, the amount of the oil of lubricating viscosity may vary widely among different embodiments, as it is dependent on the amounts of any other ingredients present in the lubricating composition. In certain embodiments, the oil of lubricating viscosity may represent a major portion of the lubricating composition. For example, the amount of the oil of lubricating viscosity present may be from 75 to 95 weight percent, such as from 80 to 95 weight percent, or from 80 to 90 weight percent, based on the total weight of the lubricating composition.

In certain embodiments, the oil of lubricating viscosity may have a kinematic viscosity measured at 100° C. of 2.4 $m^2/s$ to 6.4 $m^2/s$ according to standard test method ASTM D 445. In certain embodiments, the kinematic viscosity is from 4.0 $m^2/s$ to 5.0 $m^2/s$ or from 5.2 $m^2/s$ to 5.8 $m^2/s$ or from 6.0 $m^2/s$ to 6.5 $m^2/s$. In certain embodiments, the kinematic viscosity is 6.2 $m^2/s$, 5.6 $m^2/s$, or 4.6 $m^2/s$.

The lubricating compositions described herein may be in the form of a concentrate and/or a fully formulated lubricant. If the lubricating composition is in the form of a concentrate (which may be combined with additional oil to form, in whole or in part, a finished lubricant), the ratio of the components disclosed herein to the oil of lubricating viscosity and/or to diluent oil include the ranges of 1:99 to 99:1 by weight, or 80:20 to 10:90 by weight.

The ashless antioxidants described herein comprise 1,4-benzoxazine compounds and/or compounds derived from 1,4-benzoxazine. Benzoxazine compounds include heterocyclic compounds that have a benzene ring fused to an oxazine ring. In one embodiment, the 1,4-benzoxazine compound is substituted with a second aryl ring that shares two carbon atoms with a hetero-containing ring of the 1,4-benzoxazine compound. In another embodiment, the benzine ring and/or the oxazine ring of the 1,4-benzoxazine compound may be further substituted with hydrocarbyl groups, including a second aromatic ring fused to the oxazine ring. In some embodiments, this second ring is further substituted with a hydrocarbyl group. In one embodiment, the hydrocarbyl group includes a hydrocarbyl group having 1 to 18 carbon atoms. As used herein, the term "1,4-benzoxazine compound" is intended to mean any of the compounds described in this paragraph.

The lubricating composition of claim 1, wherein the 1,4-benzoxazine compound comprises at least one of: 10H-phenoxazine; 2, 3, 4, 4a, 10, 10a-hexahydro-1H-phenoxazine; 5H-oxazolo[4,5-b]phenoxazine; 2-phenyl-5H-oxazolo[4,5-b]phenoxazine; or hydrocarbyl-substituted derivatives thereof. In certain embodiments, the 1,4-benzoxazine compound is selected from one or more of 3, 7-dinonyl-10H-phenoxazine and 2-octyl-5H-oxazolo[4, 5-b] phenoxazine.

In certain embodiments, the 1,4-benzoxazine compound is represented by at least one of the following general formulae I:

I

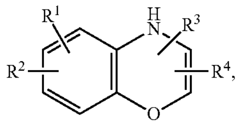

wherein, R1, R2, R3 and R4 are each independently selected from hydrogen, hydrocarbyl groups of 1 to 18 carbon atoms, and combinations thereof; or R1 and R2, taken together, form a 5- or 6-membered hydrocarbyl ring, which, optionally, contains one hetero atom and is, optionally, substituted with a hydrocarbyl group of 1 to 18 carbon atoms; or R3 and R4 taken together, form a 5- or 6-membered hydrocarbyl ring, which, optionally, contains one hetero atom and is, optionally, substituted with a hydrocarbyl group of 1 to 18 carbon atoms, wherein at least one of R1, R2, R3, and R4 is not hydrogen.

In certain embodiments, the 1,4-benzoxazine compound may be represented by the following general formulae II:

II

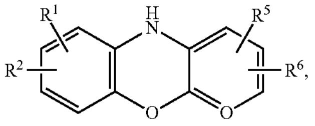

wherein, R1, R2, R5 and R6 are each independently selected from hydrogen, hydrocarbyl groups, of 1 to 18 carbon atoms, and combinations thereof, where at least one of R1, R2, R3, and R4 is not hydrogen; or R1 and R2, taken together, optionally form a 5- or 6-membered hydrocarbyl ring, which, optionally, contains one hetero atom and is, optionally, substituted with a hydrocarbyl group of 1 to 18 carbon atoms.

In one embodiment, the 1,4-benzoxazine compound may be represented by formula III:

III

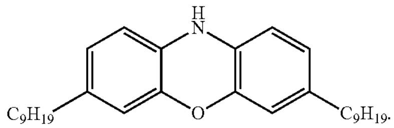

In another embodiment, the 1,4-benzoxazine compound may be represented by formula IV:

IV

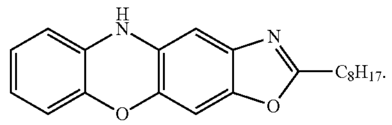

The ashless antioxidant may be present in the lubricating compositions described herein in an amount of from 0.1 to 5.0 weight percent, such as from 0.5 to 3.0 weight percent, or from 0.8 to 2.5 weight percent, or from 0.5 to 1.5 weight percent, based on the total weight of the lubricating composition.

In addition to the ashless antioxidant comprising a 1,4-benzoxazine compound described above, the lubricating compositions described herein may further comprise one or more of a polyisobutenyl succinimide dispersant, an overbased detergent, a neutral detergent, an antioxidant different from that of the ashless antioxidant described herein, an anti-wear agent, a friction modifier, a corrosion inhibitor, a polymeric viscosity modifier, and/or a foam inhibitor. In certain embodiments, fully formulated lubricating oils may contain one or more of these additives, and often a package of multiple such additives.

The lubricating compositions described herein may further comprise a dispersant. In certain embodiments, the dispersant may be a polyalkenyl succinimide dispersant. Dispersants, generally, are well known in the field of lubricants and generally include what are known as ashless dispersants and polymeric dispersants. Ashless dispersants are referred to as "ashless" because, as supplied, they do not contain metal and thus do not normally contribute to sulfated ash when added to a lubricant. However, they may interact with ambient metals once they are added to a lubricant which includes a metal-containing species. Ashless dispersants may be characterized by a polar group attached to a relatively high molecular weight hydrocarbon chain. Suitable ashless dispersants include N-substituted long chain alkenyl succinimides, having a variety of chemical structures, including those represented by the following general formula III:

III

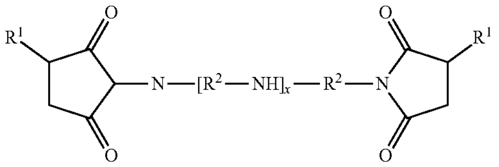

wherein, with respect to the general formula III: each $R^1$ is independently an alkyl group, such as a polyisobutylene group with a molecular weight ($M_n$) of 500-5000 g/mole based on the polyisobutylene precursor, and each $R^2$ is independently an alkylene group, such as an ethylene ($C_2H_4$) group.

Such molecules may be derived from reaction of an alkenyl acylating agent with a polyamine, and a wide variety of linkages between the two moieties is possible aside from the simple imide structure shown above, including a variety of amides and quaternary ammonium salts. In the above general formula, the amine portion is shown as an alkylene polyamine, although other aliphatic and aromatic mono- and polyamines may also be used. Also, a variety of modes of linkage of the $R^1$ groups of general formula III onto the imide structure are possible, including various cyclic linkages. The ratio of the carbonyl groups of the acylating agent to the nitrogen atoms of the amine may be 1:0.5 to 1:3, and in other instances 1:1 to 1:2.75, or 1:1.5 to 1:2.5. Succinimide dispersants are more fully described in U.S. Pat. Nos. 4,234,435, 3,172,892, and EP 0 355 895 A2/B1.

In certain embodiments, the dispersant is prepared by a process that involves the presence of small amounts of chlorine or other halogen, as described in U.S. Pat. No. 7,615,521 B2 (see, e.g., col. 4, lines 18-60 and preparative example A). Such dispersants typically have some carbocyclic structures in the attachment of the hydrocarbyl substituent to the acidic or amidic "head" group. In other embodiments, the dispersant is prepared by a thermal process involving an "ene" reaction, without the use of any chlorine or other halogen, as described in U.S. Pat. No. 7,615,521 B2; dispersants made in this manner are often derived from high vinylidene (i.e., greater than 50% terminal vinylidene) polyisobutylene (see col. 4, line 61 to col. 5, line 30 and preparative example B). Such dispersants typically do not contain the above-described carbocyclic structures at the point of attachment. In certain embodiments, the dispersant is prepared by free radical catalyzed polymerization of high-vinylidene polyisobutylene with an ethylenically unsaturated acylating agent, as described in U.S. Pat. No. 8,067,347 B2.

Some dispersants for use in the instant lubricating compositions may be derived from, as the polyolefin, high vinylidene polyisobutylene, that is, having greater than 50, 70, or 75% terminal vinylidene groups (a and 3 isomers). In certain embodiments, the succinimide dispersant may be prepared by the direct alkylation route. In other embodiments it may comprise a mixture of direct alkylation and chlorine-route dispersants.

Suitable dispersants for use in the lubricating compositions described herein include succinimide dispersants. In certain embodiments, the dispersant may be present as a single dispersant. In certain embodiments, the dispersant may be present as a mixture of two or three different dispersants, wherein at least one may optionally be a succinimide dispersant.

The succinimide dispersant may be at least one imide of an aliphatic polyamine of two to eight nitrogen atoms. The aliphatic polyamine may be an ethylenepolyamine, a propylenepolyamine, a butylenepolyamine, or mixtures thereof. In certain embodiments, the aliphatic polyamine may be ethylenepolyamine. In certain embodiments, the aliphatic polyamine may be ethylenediamine, diethylenetriamine, triethylenetetramine, tetraethylenepentamine, pentaethylenehexamine, polyamine still bottoms, or mixtures thereof.

The succinimide dispersant may be a derivative of an aromatic amine, an aromatic polyamine, or mixtures thereof. The aromatic amine may be 4-aminodiphenylamine (ADPA) (also known as N-phenylphenylenediamine), derivatives of ADPA (as described in US 2011/0306528 A1 and US 2010/0298185 A1), a nitroaniline, an aminocarbazole, an amino-indazolinone, an aminopyrimidine, 4-(4-nitrophenylazo)aniline, or combinations thereof. In certain embodiments, the dispersant is a derivative of an aromatic amine wherein the aromatic amine has at least three non-continuous aromatic rings.

The succinimide dispersant may be a derivative of a polyether amine, a polyether polyamine, or mixtures thereof. Typical polyether amine compounds contain at least one ether unit and will be chain terminated with at least one amine moiety. The polyether polyamines can be based on polymers derived from $C_2$-$C_6$ epoxides such as ethylene oxide, propylene oxide, and butylene oxide. Examples of polyether polyamines are sold under the Jeffamine® brand and are commercially available from Hunstman Corporation located in Houston, Texas.

The dispersant may also be post-treated by conventional methods, such as by reaction with any of a variety of agents. Among these agents are boron compounds, urea, thiourea, dimercaptothiadiazoles, carbon disulfide, aldehydes, ketones, carboxylic acids, hydrocarbon-substituted succinic anhydrides, maleic anhydride, nitriles, epoxides, and phosphorus compounds. In certain embodiments, the succinimide dispersant may be post-treated with boron, resulting in a borated dispersant. In certain embodiments, the succinimide dispersant comprises at least one boron-containing dispersant and at least one boron-free dispersant. In certain embodiment, the lubricating composition is free of or substantially free of a boron-containing succinimide dispersant.

The polyalkenyl succinimide dispersant may be present in an amount of from 1.2 to 4 weight percent, based on the total weight of the lubricating composition, or from 1.5 to 3.8 weight percent, based on the total weight of the lubricating composition, or from 0.5 to 4.0 weight percent, based on the total weight of the lubricating composition, or from 0.8 to 3.0 weight percent, based on the total weight of the lubricating composition, or from 1.1 to 2.3 weight percent, based on the total weight of the lubricating composition, or from 1.5 to 2.8 weight percent, based on the total weight of the lubricating composition, or from 1.2 to 3 weight percent, based on the total weight of the lubricating composition, or from 2.0 to 3.5 weight percent, based on the total weight of the lubricating composition. If a mixture of two or more dispersants comprise the succinimide dispersant, each of those dispersants may be independently present in the composition at from 0.01 to 4 weight percent, or from 0.1 to 3.5 weight percent, or from 0.5 to 3.5 weight percent, or from 1.0 to 3.0 weight percent, or from 0.5 to 2.2 weight percent, based on the total weight of the lubricating composition, with the proviso that the total amount of dispersant is as described above. In certain embodiments, the polyalkenyl succinimide dispersant is a polyisobutylene succinimide. In certain embodiments, the polyalkenyl succinimide dispersant is a polyisobutylene succinimide and is present in the lubricating composition in an amount of from 1.2 to 4 weight percent, based on the total weight of the lubricating composition.

In certain embodiments, the polyalkenyl succinimide dispersant described above is a boron-containing succinimide dispersant in an amount of from 1.2 to 4 weight percent, based on the total weight of the lubricating composition, or in treat rates described above with regard to the polyalkenyl succinimide dispersant. In another embodiment, the polyalkenyl succinimide dispersant is a mixture of boron-free and boron-containing succinimide dispersants. When both boron-containing dispersants and boron-free dispersants are present, the ratio of the one or more boron-containing dispersants to the one or more boron-free dispersants may be 4:1 to 1:4 on a weight basis, or 3:1 to 1:3, or 2:1 to 1:3, or 1:1 to 1:4 on a weight basis. In certain embodiments, one or more boron-containing dispersants is present in an amount of from 0.8 to 2.1 weight percent and one or more boron-free dispersants is present in an amount of from 0.8 to 4 weight percent, based on the total weight of the lubricating composition.

In certain embodiments, the lubricating compositions described herein may include a metal-containing detergent. The metal-containing detergent may be an overbased detergent. Overbased detergents, sometimes referred to as overbased or superbased salts, are characterized by a metal content in excess of that which would be necessary for neutralization according to the stoichiometry of the metal and the particular acidic organic compound reacted with the metal. The overbased detergent may comprise non-sulfur containing phenates, sulfur containing phenates, sulfonates, salixarates, salicylates, and/or mixtures thereof.

The overbased detergent may comprise sodium salts, calcium salts, magnesium salts, and/or mixtures thereof, of the phenates, sulfur-containing phenates, sulfonates, salixarates, and/or salicylates. Overbased phenates and salicylates typically have a total base number of from 180 to 450 TBN. Overbased sulfonates typically have a total base number of from 250 to 600, or from 300 to 500. Overbased detergents are known in the art. In certain embodiments, the sulfonate detergent may be predominantly a linear alkylbenzene sulfonate detergent having a metal ratio of at least 8, as described in paragraphs [0026] to [0037] of US 2005/0065045 A1. The linear alkylbenzene sulfonate detergent may be particularly useful for assisting in improving fuel economy. The linear alkyl group may be attached to the benzene ring anywhere along the linear chain of the alkyl group, but often in the 2, 3 or 4 position of the linear chain, and in some instances, predominantly in the 2 position, resulting in the linear alkylbenzene sulfonate detergent. The overbased detergent may be present at from 0 to 15 weight percent, or from greater than 0 to 15 weight percent, or from 0.2 to 15 weight percent, or from 0.3 to 10 weight percent, or from 0.3 to 8 weight percent, or from 0.4 to 3 weight percent, or from 0.2 to 3 weight percent, based on the total weight of the lubricating composition. For example, in a heavy-duty diesel engine, the detergent may be present at from 2 to 3 weight percent, based on the total weight of the lubricating composition. For example, in a passenger car engine, the detergent may be present at from 0.2 to 1 weight percent, based on the total weight of the lubricating composition.

Metal-containing detergents contribute sulfated ash to a lubricating composition. Sulfated ash may be determined by ASTM D874. In certain embodiments, the lubricating composition described herein may comprise a metal-containing detergent in an amount to deliver at least 0.4 weight percent sulfated ash to the total lubricating composition. In another embodiment, the metal-containing detergent is present in an amount to deliver at least 0.6 weight percent sulfated ash, or at least 0.75 weight percent sulfated ash, or at least 0.9 weigh percent sulfated ash to the total lubricating composition.

In certain embodiments, the lubricating compositions described herein may further comprise an anti-wear agent. Examples of anti-wear agents include phosphorus-containing anti-wear/extreme pressure agents (such as metal thiophosphates), phosphoric acid esters and salts thereof, phosphorus-containing carboxylic acids, phosphorus-containing esters, phosphorus-containing ethers, phosphorus-containing amides, and phosphites. In certain embodiments, a phosphorus anti-wear agent may be present in an amount to deliver from 0.01 to 0.2 weight percent, or from 0.015 to 0.15 weight percent, or from 0.02 to 0.1 weight percent, or from 0.025 to 0.08 weight percent, or from 0.01 to 0.05 weight percent phosphorus to the total lubricating composition. In certain embodiments, the anti-wear agent is a zinc dialkyldithiophosphate.

Zinc dialkyldithiophosphates may be described as primary zinc dialkyldithiophosphates or as secondary zinc dialkyldithiophosphates, depending on the structure of the alcohol used in its preparation. In certain embodiments, the lubricating compositions described herein may comprise primary zinc dialkyldithiophosphates. In certain embodiments, the lubricating compositions described herein may comprise secondary zinc dialkyldithiophosphates. In certain embodiments, the lubricating compositions described herein may comprise a mixture of primary and secondary zinc dialkyldithiophosphates, optionally wherein the ratio of primary zinc dialkyldithiophosphates to secondary zinc dialkyldithiophosphates (one a weight basis) is at least 1:1, or at least 1:1.2, or at least 1:1.5, or at least 1:2, or at least 1:10. In certain embodiments, the lubricating compositions described herein may comprise a mixture of primary and secondary zinc dialkyldithiophosphates which is at least 50 (such as at least 60, at least 70, at least 80, or at least 90) percent by weight primary zinc dialkyldithiophosphate. In certain embodiments, the lubricating compositions described herein are substantially free of primary zinc dialkyldithiophosphates, or free of primary zinc dialkyldithiophosphates.

The phosphorus anti-wear agent may be present at from 0.05 to 3 weight percent, or from 0.08 to 1.3 weight percent, or from 0.08 to 2.1 weight percent, or from 0.1 to 1.5 weight percent, or from 0.5 to 0.9 weight percent, based on the total weight of the lubricating composition.

In certain embodiments, the lubricating compositions described herein may comprise an additional antioxidant different from the ashless antioxidant comprising a 1,4-benzoxazine compound described above. Such additional antioxidants (which may also be ashless antioxidants) may comprise one or more of arylamines, diarylamines, alkylated arylamines, alkylated diaryl amines, phenols, hindered phenols, sulfurized olefins and benzazepines. Such additional antioxidants may be present at from 0.01 to 5 weight percent, or from 0.1 to 4 weight percent, or from 0.2 to 3 weight percent, or from 0.5 to 2 weight percent, based on the total weight of the lubricating composition.

The diarylamine or alkylated diarylamine may be a phenyl-α-naphthylamine (PANA), an alkylated diphenylamine, an alkylated phenylnapthylamine, or mixtures thereof. The alkylated diphenylamine may include di-nonylated diphenylamine, nonyl diphenylamine, octyl diphenylamine, di-octylated diphenylamine, di-decylated diphenylamine, decyl diphenylamine, or mixtures thereof. In certain embodiments, the diphenylamine may include nonyl diphenylamine, dinonyl diphenylamine, octyl diphenylamine, dioctyl diphenylamine, or mixtures thereof. In one embodiment the alkylated diphenylamine may include nonyl diphenylamine and/or dinonyl diphenylamine. The alkylated diarylamine may include octyl, di-octyl, nonyl, di-nonyl, decyl, or didecyl phenylnapthylamines.

The diarylamine antioxidant may be present in the lubrication composition at from 0.1 to 10 weight percent, or from 0.35 to 5 weight percent, or from 0.4 to 1.2 weight percent, or from 0.5 to 2 weight percent, based on the total weight of the lubricating composition. In certain embodiments, the lubricating composition may contains less than 0.2 weight percent, or less than 0.1 weight percent, or less than 0.05 weight percent of a diarylamine antioxidant, based on the total weight of the lubricating composition; in one embodiment, the lubricating composition is free of or substantially free of a diarylamine antioxidant.

The phenolic antioxidant may be a simple alkyl phenol, a hindered phenol, and/or coupled phenolic compounds.

The hindered phenol antioxidant may contain a secondary butyl and/or a tertiary butyl group as a sterically hindering group. The phenol group may be further substituted with a hydrocarbyl group (such as linear or branched alkyl) and/or a bridging group linking to a second aromatic group. Examples of suitable hindered phenol antioxidants include 2,6-di-tert-butyl phenol, 4-methyl-2,6-di-tert-butylphenol, 4-ethyl-2,6-di-tert-butylphenol, 4-propyl-2,6-di-tert-butylphenol, 4-butyl-2,6-di-tert-butylphenol, 4-dodecyl-2,6-di-tert-butylphenol, or butyl 3-(3,5-ditert-butyl-4-hydroxyphenyl)propanoate. In certain embodiments, the hindered phenol antioxidant may be an ester and may include, e.g., Irganox™ L-135 from BASF. In certain embodiments, the phenolic antioxidant comprises a hindered phenol. In certain embodiments, the hindered phenol is derived from 2,6-di-tert-butyl phenol.

In certain embodiments, the lubricating compositions described herein may comprise a phenolic antioxidant in a range of from 0.01 to 5 weight percent, or from 0.1 to 4 weight percent, or from 0.2 to 3 weight percent, or from 0.5 to 2 weight percent, based on the total weight of the lubricating composition.

Sulfurized olefins are well-known commercial materials, and those which are substantially nitrogen-free, that is, not containing nitrogen functionality, are readily available. The olefinic compounds which may be sulfurized are diverse in nature. They contain at least one olefinic double bond, which is defined as a non-aromatic double bond; that is, one connecting two aliphatic carbon atoms. These materials generally have sulfide linkages having 1 to 10 sulfur atoms, for instance, 1 to 4, or 1, or 2.

In some embodiments, the ashless antioxidants may be a benzazepine compound and/or a compound derived from benzazepine. Benzazepine compounds are heterocyclic compounds containing a benzene ring fused to an azepine ring. Benzazepine compounds may be further substituted with hydrocarbyl groups, including dibenzazepine compounds comprising a second aromatic ring fused to the azepine ring. Benzazepine compounds may also be selected such that the azepine ring may be unsaturated, or fully or partially saturated. In certain embodiments, the azepine ring may further contain a heteroatom, such as oxygen, sulfur, and/or nitrogen.

The additional (such as ashless) antioxidants described above may be used separately or in combination. In certain embodiments, two or more different additional antioxidants may be used in combination, such that there is at least 0.1 weight percent of each of the at least two antioxidants, and optionally wherein the combined amount of the additional antioxidants is 0.5 to 5 weight percent, based on the total weight of the lubricating composition. In certain embodiments, there may be from 0.25 to 3 weight of each additional antioxidant, based on the total weight of the lubricating composition.

In certain embodiments, the lubricating compositions described herein may comprise a molybdenum compound. The molybdenum compound may be molybdenum dialkyldithiophosphates, molybdenum dithiocarbamates, amine salts of molybdenum compounds, or mixtures thereof. The molybdenum compound may provide the lubricating composition with from 0 to 1000 ppm, or from 5 to 1000 ppm, or from 10 to 750 ppm, or from 5 to 300 ppm, or from 20 to 250 ppm, or from 350 to 900 ppm molybdenum, based on the total lubricating composition.

The lubricating compositions described herein may further comprise a polymeric viscosity modifier. It is known that polymeric viscosity modifiers may be functionalized or derivatized; functionalized polymeric viscosity modifiers are also called dispersant viscosity modifiers (DVM). The polymeric viscosity modifiers may be olefin (co)polymers, poly(meth)acrylate (PMA), or mixtures thereof. In certain embodiments, the polymeric viscosity modifier is an olefin (co)polymer.

The olefin polymer may be derived from isobutylene or isoprene. In certain embodiments, the olefin polymer is prepared from ethylene and a higher olefin within the range of $C_3$-$C_{10}$ alpha-mono-olefins; for example, the olefin polymer may be prepared from ethylene and propylene.

In certain embodiments, the olefin polymer may be a polymer of from 15 to 80 (such as from 30 to 70) mole percent ethylene, and from 20 to 85 (such as from 30 to 70) mole percent $C_3$ to $C_{10}$ mono-olefins, such as propylene. Terpolymer variations of the olefin copolymer may also be used and may contain up to 15 mol percent of a non-conjugated diene or triene. Non-conjugated dienes or trienes may have 5 to 14 carbon atoms. The non-conjugated diene or triene monomers may be characterized by the presence of a vinyl group in the structure and can include cyclic and bicycle compounds. Representative dienes include 1,4-hexadiene, 1,4-cyclohexadiene, dicyclopentadiene, 5-ethyldiene-2-norbornene, 5-methylene-2-norbornene, 1,5-heptadiene, and 1,6-octadiene.

In certain embodiments, the olefin copolymer may be a copolymer of ethylene, propylene, and butylene. The polymer may be prepared by polymerizing a mixture of monomers comprising ethylene, propylene, and butylene. These polymers may be referred to as copolymers or terpolymers. The terpolymer may comprise from 5 to 20 mole percent, or from 5 to 10 mole percent, structural units derived from ethylene; from 60 to 90 mole percent, or from 60 mole percent to 75 mole percent, structural units derived from propylene; and from 5 to 30 mole percent, or from 15 to 30 mole percent, structural units derived from butylene. The butylene may comprise any isomers or mixtures thereof, such as n-butylene, iso-butylene, or a mixture thereof. The butylene may comprise butene-1. Commercial sources of butylene may comprise butene-1 as well as butene-2 and butadiene. The butylene may comprise a mixture of butene-1 and isobutylene wherein the weight ratio of butene-1 to isobutylene is about 1:0.1 or less. The butylene may comprise butene-1 and be free of or substantially free of isobutylene.

In certain embodiments, the olefin copolymer may be a copolymer of ethylene and butylene. The polymer may be prepared by polymerizing a mixture of monomers comprising ethylene and butylene, wherein the monomer composition is free of or substantially free of propylene monomers (i.e., contains less than 1 weight percent of intentionally added propylene monomer). The copolymer may comprise from 30 to 50 mole percent structural units derived from butylene; and from 50 to 70 mole percent structural units derived from ethylene. The butylene may comprise a mixture of butene-1 and isobutylene wherein the weight ratio of butene-1 to isobutylene is about 1:0.1 or less. The butylene may comprise butene-1 and be free of or substantially free of isobutylene.

Useful olefin polymers, such as ethylene-α-olefin copolymers, have a number average molecular weight ranging from 4,500 to 500,000 g/mole, for example, 5,000 to 100,000 g/mole, or 7,500 to 60,000 g/mole, or 8,000 to 45,000 g/mole.

In certain embodiments, the lubricating compositions described herein may comprise a poly(meth)acrylate polymeric viscosity modifier. As used herein, the term "(meth) acrylate" and its cognates means methacrylate and/or acrylate.

In certain embodiments, the poly(meth)acrylate polymer is prepared from a monomer mixture comprising (meth) acrylate monomers having alkyl groups of varying length. The (meth)acrylate monomers may contain alkyl groups that are straight chain or branched chain groups. The alkyl groups may contain 1 to 24 carbon atoms, for example 1 to 20 carbon atoms.

The poly(meth)acrylate polymers may be formed from monomers derived from saturated alcohols, such as methyl (meth)acrylate, ethyl (meth)acrylate, propyl (meth)acrylate, butyl (meth)acrylate, 2-methylpentyl (meth)acrylate, 2-propylheptyl (meth)acrylate, 2-butyloctyl (meth)acrylate, 2-ethylhexyl (meth)acrylate, octyl (meth)acrylate, nonyl (meth)acrylate, isooctyl (meth)acrylate, isononyl (meth) acrylate, 2-tert-butylheptyl (meth)acrylate, 3-isopropylheptyl (meth)acrylate, decyl (meth)acrylate, undecyl (meth) acrylate, 5-methylundecyl (meth)acrylate, dodecyl (meth) acrylate, 2-methyldodecyl (meth)acrylate, tridecyl (meth) acrylate, 5-methyltridecyl (meth)acrylate, tetradecyl (meth) acrylate, pentadecyl (meth)acrylate, hexadecyl (meth) acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth), acrylate, (meth)acrylates derived from unsaturated alcohols (such as oleyl (meth)acrylate), and/or cycloalkyl (meth)acrylates (such as 3-vinyl-2-butylcyclohexyl (meth) acrylate or bornyl (meth)acrylate).

Other examples of monomers include alkyl (meth)acrylates with long-chain alcohol-derived groups which may be obtained, for example, by reaction of a (meth)acrylic acid (by direct esterification) or methyl (meth)acrylate (by transesterification) with long-chain fatty alcohols, in which reaction a mixture of esters such as (meth)acrylate with alcohol groups of various chain lengths is generally obtained. These fatty alcohols include Oxo Alcohol® 7911, Oxo Alcohol® 7900 and Oxo Alcohol® 1100 from Monsanto; Alphanol® 79 from ICI; Nafol® 1620, Alfol® 610 and Alfol® 810 from Sasol; Epal® 610 and Epal® 810 from Ethyl Corporation; Linevol® 79, Linevol® 911 and Dobanol® 25 L from Shell AG; Lial® 125 from Condea Augusta, Milan; Dehydad® and Lorol® from Cognis, and Linopol® 7-11 and Acropol® 91 from Ugine Kuhlmann.

In certain embodiments, the poly(meth)acrylate polymer comprises a dispersant monomer; dispersant monomers include those monomers which may copolymerize with (meth)acrylate monomers and contain one or more heteroatoms in addition to the carbonyl group of the (meth)acrylate. The dispersant monomer may contain a nitrogen-containing group, an oxygen-containing group, or mixtures thereof.

The nitrogen-containing compound may be a (meth) acrylamide or a nitrogen containing (meth)acrylate monomer. Examples of a suitable nitrogen-containing compounds include N,N-dimethylacrylamide, N-vinyl carbonamides (such as N-vinyl-formamide), vinyl pyridine, N-vinylacetoamide, N-vinyl propionamides, N-vinyl hydroxy-acetoamide, N-vinyl imidazole, N-vinyl pyrrolidinone, N-vinyl caprolactam, dimethylaminoethyl acrylate (DMAEA), dimethylaminoethyl methacrylate (DMAEMA), dimethylaminobutyl acrylamide, dimethylaminopropyl meth-acrylate (DMAPMA), dimethylaminopropyl acrylamide, dimethylaminopropyl methacrylamide, dimethylaminoethyl acrylamide, or mixtures thereof.

Dispersant monomers may be present in an amount up to 5 mole percent of the monomer composition of the (meth) acrylate polymer. In one embodiment, the poly(meth)acrylate is present in an amount 0 to 5 moel percent, or 0.5 to 4 mole percent, or 0.8 to 3 mol percent, of the polymer composition. In certain embodiments, the poly(meth)acrylate is free of or substantially free of dispersant monomers.

In certain embodiments, the poly(meth)acrylate comprises a block copolymer or tapered block copolymer. Block copolymers are formed from a monomer mixture comprising one or more (meth)acrylate monomers, wherein, for example, a first (meth)acrylate monomer forms a discrete block of the polymer joined to a second discrete block of the polymer formed from a second (meth)acrylate monomer. While block copolymers have substantially discrete blocks formed from the monomers in the monomer mixture, a tapered block copolymer may be composed of, at one end, a relatively pure first monomer and, at the other end, a relatively pure second monomer, while the middle of the tapered block copolymer is more of a gradient composition of the two monomers.

In certain embodiments, the poly(meth)acrylate polymer (P) may be a block or tapered block copolymer that comprises at least one polymer block (B1) that is insoluble or substantially insoluble in the base oil and a second polymer block (B2) that is soluble or substantially soluble in the base oil.

In certain embodiments, the poly(meth)acrylate polymers may have an architecture selected from linear, branched, hyper-branched, cross-linked, star (also referred to as "radial"), or combinations thereof. Star or radial refers to multi-armed polymers. Such polymers include (meth)acrylate-containing polymers comprising three or more arms or branches, which, in some embodiments, may contain at least 20 (such as at least 50, 100, 200, 350, 500, or 1000) carbon atoms. The arms are generally attached to a multivalent organic moiety which acts as a "core" or "coupling agent." The multi-armed polymer may be referred to as a radial or star polymer, or even a "comb" polymer, or a polymer otherwise having multiple arms or branches as described herein.

Linear poly(meth)acrylates, random, block or otherwise, may have weight average molecular weight (Mw) of from 1000 to 400,000 Daltons, from 1000 to 150,000 Daltons, or from 15,000 to 100,000 Daltons. In certain embodiments, the poly(meth)acrylate may be a linear block copolymer with a Mw of from 5,000 to 40,000 Daltons, or from 10,000 to 30,000 Daltons.

Radial, cross-linked or star copolymers may be derived from linear random or di-block copolymers with molecular weights as described above. A star polymer may have a weight average molecular weight of from 10,000 to 1,500, 000 Daltons, or from 40,000 to 1,000,000 Daltons, or from 300,000 to 850,000 Daltons.

The lubricating compositions described herein may comprise from 0.05 to 2 weight percent, or from 0.08 to 1.8 weight percent, or from 0.1 to 1.2 weight percent, of the one or more polymeric viscosity modifiers as described herein, based on the total weight of the lubricating composition.

In certain embodiments, the polymeric viscosity modifier may include a DVM. The DVM may be present at from 0 to 5 weight percent, or from 0 to 4 weight percent, or from greater than 0 to 5 weight percent, or from greater than 0 to 4 weight percent, or from 0.05 to 2 weight percent, based on the total weight of the lubricating composition.

Suitable DVMs include: functionalized polyolefins, for example, ethylene-propylene copolymers that have been functionalized with an acylating agent such as maleic anhydride and an amine; polymethacrylates functionalized with an amine; or esterified styrene-maleic anhydride copolymers reacted with an amine. Descriptions of DVMs are provided in WO 2006/015130 A1, or U.S. Pat. Nos. 4,863,623, 6,107,257, 6,107,258, and 6,117,825. In certain embodiments, the DVM may include those described in U.S. Pat. No. 4,863,623 (see column 2, line 15 to column 3, line 52) or in WO 2006/015130 A1 (see page 2, paragraph [0008] and preparative examples are described at paragraphs [0065] to [0073]).

Suitable amines for formation of DVMs include aliphatic amines, aliphatic polyamines, aromatic amines, aromatic polyamines, polyether compounds, polyetheramines (such as those described above), and combinations thereof. The aliphatic polyamine may be an ethylenepolyamine, a propylenepolyamine, a butylenepolyamine, or mixtures thereof. In certain embodiments, the aliphatic polyamine may be ethylenepolyamine. In certain embodiments the aliphatic polyamine may be ethylenediamine, diethylenetriamine, triethylenetetramine, tetraethylenepentamine, pentaethylenehexamine, polyamine still bottoms, or mixtures thereof.

The aromatic amine may be 4-aminodiphenylamine (ADPA) (also known as N-phenylphenylenediamine), derivatives of ADPA (as described in US 2011/0306528 A1 and US 2010/0298185 A1), a nitroaniline, an aminocarbazole, an amino-indazolinone, an aminopyrimidine, 4-(4-nitrophenylazo)aniline, or combinations thereof. In certain embodiments, the DVM may be a derivative of an aromatic amine, optionally wherein the aromatic amine has at least three non-continuous aromatic rings.

The DVM may be a derivative of a polyether amine or polyether polyamine. Suitable polyether amine compounds may contain at least one ether unit and may be chain terminated with at least one amine moiety. The polyether polyamines can be based on polymers derived from $C_2$-$C_6$ epoxides such as ethylene oxide, propylene oxide, and butylene oxide. Examples of commercially-available polyether polyamines are sold under the Jeffamine® brand and are commercially available from Hunstman Corporation located in Houston, Texas.

In certain embodiments, the lubricating compositions described herein may further comprise a friction modifier. Examples of suitable friction modifiers include long chain fatty acid derivatives of amines, fatty esters, or epoxides; fatty imidazolines, such as condensation products of carboxylic acids and polyalkylene-polyamines; amine salts of alkylphosphoric acids; fatty alkyl tartrates; fatty alkyl tartrimides; and/or fatty alkyl tartramides. The term fatty, as used herein, may mean having a $C_8$-$C_{22}$ linear alkyl group.

These friction modifiers may also encompass materials such as sulfurized fatty compounds and olefins, molybdenum dialkyldithiophosphates, molybdenum dithiocarbamates, sunflower oil, and/or a monoester of a polyol and an aliphatic carboxylic acid.

In certain embodiments, the friction modifier may comprise at least one of long chain fatty acid derivatives of amines, long chain fatty esters, or long chain fatty epoxides; fatty imidazolines; amine salts of alkylphosphoric acids; fatty alkyl tartrates; fatty alkyl tartrimides; or fatty alkyl tartramides.

In certain embodiments, the friction modifier may be a long chain fatty acid ester. In certain embodiments the long chain fatty acid ester may be a mono-ester, a diester, or a mixture thereof, and in certain embodiments the long chain fatty acid ester may be a triglyceride. In certain embodiments, the friction modifier may be glycerol mono-oleate.

The friction modifier may be present at from 0 to 6 weight percent, or from 0.05 to 4 weight percent, or from 0.1 to 2 weight percent, based on the total weight of the lubricating composition.

Other performance additives, such as corrosion inhibitors, include those described in WO 2006/047486 A1, octyl octanamide, condensation products of dodecenyl succinic acid or anhydride and a fatty acid (such as oleic acid) with a polyamine may be present in the lubricating compositions described herein. In certain embodiments, the corrosion inhibitors include Synalox® (a registered trademark of The Dow Chemical Company) corrosion inhibitors. Synalox® corrosion inhibitors may be a homopolymer or copolymer of propylene oxide. The Synalox®. corrosion inhibitors are described in more detail in a product brochure with Form No. 118-01453-0702 AMS, published by The Dow Chemical Company, entitled "SYNALOX Lubricants, High-Performance Polyglycols for Demanding Applications".

The lubricating compositions described herein may further comprise: metal deactivators, including derivatives of benzotriazoles (typically tolyltriazole), dimercaptothiadiazole derivatives, 1,2,4-triazoles, benzimidazoles, 2-alkyldithiobenzimidazoles, and/or 2-alkyldithiobenzothiazoles; foam inhibitors, including copolymers of ethyl acrylate and 2-ethylhexylacrylate, and/or copolymers of ethyl acrylate and 2-ethylhexylacrylate and vinyl acetate; demulsifiers, including trialkyl phosphates, polyethylene glycols, polyethylene oxides, polypropylene oxides, and/or (ethylene oxide/propylene oxide) polymers; and pour point depressants, including esters of maleic anhydride-styrene, polymethacrylates, polyacrylates, and/or polyacrylamides.

Suitable our point depressants may include polyalphaolefins, esters of maleic anhydride-styrene, poly(meth)acrylates, polyacrylates, and/or polyacrylamides.

In certain embodiments the lubricating compositions described herein may have a composition as described in the following tables:

| Additive | Embodiments (wt %) A | B | C |
|---|---|---|---|
| 1,4-benzoxazine Compound | 0.1 to 5.0 | 0.5 to 3.0 | 0.8 to 2.5 |
| Polyalkenyl Succinimide Dispersant | 1.2 to 8 | 1.5 to 5 | 2 to 3.4 |
| Anti-wear Agent(s) | 0.15 to 4 | 0.2 to 2 | 0.5 to 1.5 |
| Additional Ashless Antioxidant(s) | 0 to 6 | 0.6 to 3 | 0.8 to 2.5 |
| Metal Detergent(s) | 0 to 5 | 0.45 to 2.5 | 0.8 to 2 |
| Viscosity Modifier(s) | 0 or 0.1 to 4.5 | 0.5 to 3 | 0.8 to 1.8 |
| Dispersant Viscosity Modifier(s) | 0 or 0.1 to 4.5 | 0 or 0.1 to 2.5 | 0.5 to 1.6 |
| Friction Modifier(s) | 0 or 0.05 to 2 | 0.05 to 1.6 | 0.1 to 1.2 |
| Any Other Performance Additive(s) | 0 or 0.05 to 6 | 0 or 0.05 to 3 | 0 or 0.05 to 1.8 |
| Other Oil of Lubricating Viscosity | Balance to 100% | | |

| Additive | Embodiments (wt %) A | B | C |
|---|---|---|---|
| Compound of Formula III | 0.1 to 5.0 | 0.5 to 3.0 | 0.8 to 2.5 |
| Polyalkenyl Succinimide Dispersant | 1.2 to 8 | 1.5 to 5 | 2 to 3.4 |
| Anti-wear Agent(s) | 0.15 to 4 | 0.2 to 2 | 0.5 to 1.5 |
| Additional Ashless Antioxidant(s) | 0 to 6 | 0.6 to 3 | 0.8 to 2.5 |
| Metal Detergent(s) | 0 to 5 | 0.45 to 2.5 | 0.8 to 2 |
| Viscosity Modifier(s) | 0 or 0.1 to 4.5 | 0.5 to 3 | 0.8 to 1.8 |
| Dispersant Viscosity Modifier(s) | 0 or 0.1 to 4.5 | 0 or 0.1 to 2.5 | 0.5 to 1.6 |
| Friction Modifier(s) | 0 or 0.05 to 2 | 0.05 to 1.6 | 0.1 to 1.2 |
| Any Other Performance Additive(s) | 0 or 0.05 to 6 | 0 or 0.05 to 3 | 0 or 0.05 to 1.8 |
| Other Oil of Lubricating Viscosity | Balance to 100% | | |

| Additive | Embodiments (wt %) A | B | C |
|---|---|---|---|
| Compound of Formula IV | 0.1 to 5.0 | 0.5 to 3.0 | 0.8 to 2.5 |
| Polyalkenyl Succinimide Dispersant | 1.2 to 8 | 1.5 to 5 | 2 to 3.4 |
| Anti-wear Agent(s) | 0.15 to 4 | 0.2 to 2 | 0.5 to 1.5 |
| Additional Ashless Antioxidant(s) | 0 to 6 | 0.6 to 3 | 0.8 to 2.5 |
| Metal Detergent(s) | 0 to 5 | 0.45 to 2.5 | 0.8 to 2 |
| Viscosity Modifier(s) | 0 or 0.1 to 4.5 | 0.5 to 3 | 0.8 to 1.8 |
| Dispersant Viscosity Modifier(s) | 0 or 0.1 to 4.5 | 0 or 0.1 to 2.5 | 0.5 to 1.6 |
| Friction Modifier(s) | 0 or 0.05 to 2 | 0.05 to 1.6 | 0.1 to 1.2 |
| Any Other Performance Additive(s) | 0 or 0.05 to 6 | 0 or 0.05 to 3 | 0 or 0.05 to 1.8 |
| Other Oil of Lubricating Viscosity | Balance to 100% | | |

The 1,4-benzoxazine compounds described herein may be used in lubricant compositions formulated to lubricate a mechanical device. Such mechanical devices include, without limitation, an internal combustion engine (such as, for example, a spark ignited internal combustion engine, or a compression ignition internal combustion engine), and a driveline device (such as an automatic transmission, manual transmission, dual clutch transmissions, or an axle or differential). The compression ignition internal combustion engine may include a heavy-duty diesel engine.

Diesel engines may be classified by their Gross Vehicle Weight Rating (GVWR). The GVWR includes the maximum rated weight of the vehicle and cargo, including passengers. The GVWR may be applied to trucks or trailers, but not the two combined, which is a separate rating referred to as the Gross Combined Weight Rating (GCWR). The GVWR's for various classes of diesel engines are set forth in the following table:

| Class | GVWR (lbs) |
|---|---|
| Class 1 | 0-6,000 lbs |
| Class 2A | 6,001-8,500 lbs |
| Class 2B | 8,501-10,000 lbs |
| Class 3 | 10,001-14,000 lbs |
| Class 4 | 14,001-16,000 lbs |
| Class 5 | 16,001-19,500 lbs |
| Class 6 | 19,5001-26,000 lbs |
| Class 7 | 26,001-33,000 lbs |
| Class 8 | Over 33,000 lbs |

Light duty vehicles are classified as those falling in Class 1 to 3. Class 2A vehicles are typically called "light duty" and class 2B vehicles are often called "light heavy duty" vehicles. Medium duty vehicles refer to those falling into Classes 4 to 6. Heavy-Duty vehicles are those classified in Class 7 and Class 8.

Lubricant compositions described herein having the disclosed ashless antioxidant comprising a 1,4-benzoxazine compound may be used in lubricants for diesel engines in all of Class 1 through Class 8 engines. In certain embodiments, the lubricant compositions are used in Class 8 engines.

EXAMPLES

The subject matter disclosed herein may be better understood with reference to the following examples, which are set forth merely to further illustrate the subject matter disclosed herein. The illustrative examples should not be construed as limiting the subject matter in any manner.

A series of 1,4-benzoxazine compounds are evaluated for their ability to reduce oxidative degradation of lubricating compositions. The procedure to alkylate commercially available selected 1,4-benzoxazine is described below, and examples of suitable 1,4-benzoxazine compounds are summarized below (Table 1).

Example 1

A 500 mL, 4-neck flask was equipped with an overhead stirrer, nitrogen surface tube supplying 0.1 cfh N2, and a Dean-Stark trap topped with a water condenser. To the flask was charged with propylene trimer (102 g, 0.82 mol). The flask was heated to 85° C. and 10H-phenoxazine (50 g, 0.27 mol) was then charged and slurried in the flask. The reaction was further heated to 100° C. and acidic clay (15 g) was then charged. The reaction was heated to reflux at 150° C. and held for 9 h. The reaction was diluted in hexane and filtered to remove the catalyst. The residual olefin was stripped at 170° C. and filtered again to give the dinonyl-10H-phenoxazine product as a red, viscous oil (103 g, 87.3% theoretical yield). % N~3.17% (Theory~3.2%) GC-MS analysis indicated the product yield was 71.3 wt % dinonyl-10H-phenoxazine.

Example 2

A 100 mL, 2-neck flask was fitted with a Dean-Stark trap and a Claisen adapter topped with an $N_2$ line and thermocouple. 2-amino-3H-phenoxazin-3-one (6 g, 28 mmol), nonanal (4.4 g, 31 mmol), and toluene (80 g) were added to the flask. A few drops of acetic acid were added, and the flask was then refluxed 4 hours. The solvent was then removed, and the residue was dissolved in ethyl acetate (100 g). The product was extracted with sodium bisulfite, water, and brine then dried to give the product as a dark red oil (5.0 g, 52.5% theoretical yield) 2-octyl-5H-oxazolo[4,5-b]phenoxazine.

Lubricating compositions: A series of 5W-30 lubricant compositions were prepared with the various 1,4-benzoxazine compounds described herein as well as conventional crankcase additives such as ashless polyisobutenylsuccinimide dispersant, overbased alkaline earth metal detergent, zinc dialkyl dithiophosphate (ZDDP), additional ashless antioxidant, polymeric viscosity modifiers, and other common additives, as shown in Table 2.

TABLE 2[1]

| | EX1 | EX2 | EX3 | EX4 | EX5 |
|---|---|---|---|---|---|
| Group III Base Oil | Balance to 100% | | | | |
| Nonylated diphenylamine | 0.80 | 1.50 | 0 | 0 | 0 |
| 3,7-dinonyl-10H-phenoxazine Example 1 | 0 | 0 | 0.80 | 1.50 | 0 |
| 2-octyl-5H-oxazolo [4,5-b] phenoxazine Example 2 | 0 | 0 | 0 | 0 | 1.50 |
| PIBsuccinimide Dispersant[2] | 4.785 | 4.785 | 4.785 | 4.785 | 4.785 |
| Borated PIBsuccinimide Dispersant[3] | 5 | 5 | 5 | 5 | 5 |
| Magnesium Sulfonate[4] | 0.50 | 0.50 | 0.50 | 0.50 | 0.50 |
| Calcium Salicylate[5] | 2 | 2 | 2 | 2 | 2 |
| ZDDP - Secondary C3/C6 | 0.80 | 0.80 | 0.80 | 0.80 | 0.80 |
| Sulfurized olefin | 0.50 | 0.50 | 0.50 | 0.50 | 0.50 |
| Oxyalkylatedphenol | 2 | 2 | 2 | 2 | 2 |
| Styrene-diene VM | 6.70 | 6.70 | 6.70 | 6.70 | 6.70 |
| Other Additives[6] | 0.20 | 0.20 | 0.20 | 0.20 | 0.20 |
| Calcium (ppm) | 1220 | 1220 | 1215 | 1220 | 1220 |
| Magnesium (ppm) | 490 | 480 | 460 | 470 | 480 |
| Phosphorus (ppm) | 830 | 835 | 830 | 830 | 860 |
| Sulfur (ppm) | 2550 | 2580 | 2530 | 2540 | 2680 |
| KV100 (ASTM D445- 100° C.), cSt | 9.803 | 9.841 | 9.843 | 9.950 | — |
| TBN (ASTM D4739), mg KOH/g | 6.6 | 6.5 | 6.8 | 6.8 | — |

*Calculated value
[1]All treat rates are oil free, unless otherwise indicated
[2]Polyisobutenyl succinimide made from high vinylidene PIB (TBN 26 mg KOH/g)
[3]Polyisobutenyl succinimide made from high vinylidene PIB (TBN 26 mg KOH/g)
[4]Overbased magnesium alkylbenzene sulfonate (TBN 700 mg KOH/g)
[5]Overbased calcium alkylsalicylate (TBN 300 mg KOH/g)
[6]Other additives include pourpoint depressant and foam inhibitor Table 3 illustrates the results of the Komatsu Hot Tube Test and Pressure Differential Scanning Calorimetry. Deposit control is measured by the Komatsu Hot Tube (KHT) test, which employs heated glass tubes through which sample lubricating composition is pumped, approximately 5 mL total sample, typically at 0.31 mL/hour for an extended period of time, such as 16 hours, with an air flow of 10 mL/minute. The glass tube is rated at the end of test for deposits on a scale of 0 (very heavy varnish) to 10 (no varnish).

Thin-film oxidative stability (antioxidancy performance) is measured according to the ACEA E5 oxidation bench test, CEC L-85-99, 4 Nov. 2014, "Hot Surface Oxidation—Pressure Differential Scanning calorimeter (PDSC). In the test, 2 mg of a sample is heated to between 50° C. and 210° C., then held at that temperature for up to 2 hours in a closed system at 100 psi (~0.69 MPa) overpressure. The oxidative induction time, expressed in minutes, is the onset time (until the oil breaks and oxidation begins) observed from achieving the isothermal temperature. Higher values are thus better. The results of the KHT and PDSC tests are shown for Examples EX1 through EX5 in Table 3 below:

TABLE 3

| | EX1 | EX2 | EX3 | EX4 | EX5 |
|---|---|---|---|---|---|
| Komatsu Hot Tube (KHT) at 280° C. | 7 | 7 | 7 | 6 | 5.5 |
| Pressure Differential Scanning Calorimetry (L-85-99), min | 119.2 | 173.6 | 99.3 | 206.7 | 153 1 |

Except in the Examples, or where otherwise explicitly indicated or required by context, all numerical quantities in this description specifying amounts of materials, reaction conditions, molecular weights, number of carbon atoms, and the like, are to be understood as modified by the word "about". As used herein, the term "about" means that a value of a given quantity is within ±20% of the stated value. In other embodiments, the value is within ±15% of the stated value. In other embodiments, the value is within ±10% of the stated value. In other embodiments, the value is within ±5% of the stated value. In other embodiments, the value is within ±2.5% of the stated value. In other embodiments, the value is within ±1% of the stated value. In other embodiments, the value is within a range of the explicitly described value which would be understood by those of ordinary skill, based on the disclosures provided herein, to perform substantially similarly to compositions including the literal amounts described herein.

It is to be understood that the upper and lower amount, range, and ratio limits set forth herein may be independently combined, and that any amount within a disclosed range is contemplated to provide a minimum or maximum of a narrower range in alternative embodiments (with the proviso, of course, that the minimum amount of a range must be lower than the maximum amount of the same range). Similarly, the ranges and amounts for each element of the subject matter disclosed herein may be used together with ranges or amounts for any of the other elements.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and components within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used herein is for the purpose of describing particular embodiments only and is not intended to be limiting.

What is claimed is:

1. A lubricating composition comprising an oil of lubricating viscosity and an oil soluble 1,4-benzoxazine compound, wherein the 1,4 benzoxazine compound is selected from the group consisting of Formula IV

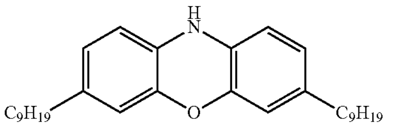

or

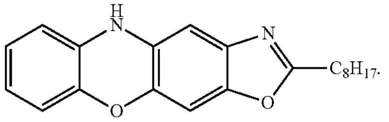

2. The lubricating composition of claim 1, wherein the 1,4-benzoxazine compound is present in the lubricating composition in an amount 0.1 to 5.0 weight percent, or 0.5 to 3.0 weight percent, or 0.8 to 2.5 weight percent, based on the total weight of the lubricating composition.

3. The lubricating composition of claim 1, wherein the lubricating composition comprises at least one additional lubricant additive comprising at least one of an ashless polyisobutenyl succinimide dispersant, an overbased or neutral metal-based detergent, an anti-wear agent, a polymeric viscosity modifier, or an ashless antioxidant different from the 1,4-benzoxazine compound.

4. The lubricating composition of claim 3, wherein the ashless polyisobutenyl succinimide dispersant is present in the lubricating composition in an amount of from 0.5 to 4.0 weight percent, or 0.8 to 3.0 weight percent, or 1.1 to 2.3 weight percent, or 1.5 to 2.8 weight percent, based on the total weight of the lubricating composition.

5. The lubricating composition of claim 3, wherein the metal-based detergent comprises at least one of a neutral alkaline earth metal detergent or an overbased alkaline earth metal detergent, in an amount of from 0.2 to 15 weight percent, or 0.3 to 10 weight percent, or 0.3 to 8 weight percent, or 0.4 to 3 weight percent, based on the total weight of the lubricating composition.

6. The lubricating composition of claim 5, wherein the at least one of a neutral alkaline earth metal detergent or an overbased alkaline earth metal detergent comprises at least one of an alkylbenzene sulfonate detergent, a sulfur-coupled phenate detergent, or an alkylsalicylate detergent.

7. The lubricating composition of claim 3, wherein at least one anti-wear agent is present in an amount of from 0.05 to 3 weight percent, or 0.08 to 1.3 weight percent, or 0.08 to 2.1 weight percent, or 0.1 to 1.5 weight percent, or 0.5 to 0.9 weight percent, based on the total weight of the lubricating composition.

8. The lubricating composition of claim 7, wherein the at least one anti-wear agent comprises a phosphorus-containing compound in an amount effective to deliver 200 to 1200 ppm phosphorus to the lubricating composition.

9. The lubricating composition of claim 7, wherein the at least one anti-wear agent comprises a zinc dialkyl dithiophosphate.

10. The lubricating composition of claim 3, wherein the ashless antioxidant different from the 1,4-benzoxazine compound is present in an amount of from 0.01 to 5 weight percent, or 0.1 to 4 weight percent, or 0.2 to 3 weight percent, or 0.5 to 2 weight percent, based on the total weight of the lubricating composition.

11. The lubricating composition of claim 1, wherein the lubricating composition comprises less than 0.1 weight percent of a diarylamine antioxidant.

12. The lubricating composition of claim 1, wherein the lubricating composition is substantially free of a diarylamine antioxidant.

13. A method of lubricating an internal combustion engine comprising supplying to the internal combustion engine the lubricating composition of claim 1.

14. A method of improving the oxidative resistance of a crankcase lubricant, wherein the method comprises lubricating the crankcase with the lubricating composition of claim 1.

* * * * *